United States Patent
Miyaki et al.

(10) Patent No.: US 7,365,041 B2
(45) Date of Patent: Apr. 29, 2008

(54) METHOD FOR PRODUCING AMMOXIDATION CATALYST

(75) Inventors: Kenichi Miyaki, Yokohama (JP); Motoo Yanagita, Yokohama (JP); Kunio Mori, Yokohama (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 294 days.

(21) Appl. No.: 10/490,219

(22) PCT Filed: Sep. 25, 2002

(86) PCT No.: PCT/JP02/09832

§ 371 (c)(1),
(2), (4) Date: Apr. 1, 2004

(87) PCT Pub. No.: WO03/033139

PCT Pub. Date: Apr. 24, 2003

(65) Prior Publication Data

US 2004/0248734 A1    Dec. 9, 2004

(30) Foreign Application Priority Data

Oct. 11, 2001  (JP)  ................. 2001-314054

(51) Int. Cl.
*B01J 23/31* (2006.01)

(52) U.S. Cl. .................. 502/311; 502/206; 502/211; 502/212; 502/215; 502/248; 502/255; 502/302; 502/303; 502/304; 502/312; 502/313; 502/314; 502/315; 502/316; 502/317; 502/318; 502/319; 502/321

(58) Field of Classification Search ................ 502/206, 502/211, 212, 215, 248, 255, 302–304, 311–319, 502/321
See application file for complete search history.

(56) References Cited

U.S. PATENT DOCUMENTS

| | | | | |
|---|---|---|---|---|
| 4,826,802 A | * | 5/1989 | Sasaki et al. | ............... 502/206 |
| 4,978,765 A | * | 12/1990 | Sasaki et al. | ............... 558/324 |
| 5,059,573 A | * | 10/1991 | Sasaki et al. | ............... 502/205 |
| 5,071,814 A | * | 12/1991 | Sasaki et al. | ............... 502/205 |
| 5,094,990 A | * | 3/1992 | Sasaki et al. | ............... 502/214 |
| 5,132,269 A | * | 7/1992 | Sasaki et al. | ............... 502/205 |
| 5,139,988 A | * | 8/1992 | Sasaki et al. | ............... 502/206 |
| 5,834,394 A | * | 11/1998 | Chen et al. | ................. 502/302 |
| 5,840,648 A | | 11/1998 | Suresh et al. | |
| 6,100,215 A | | 8/2000 | Sasaki et al. | |
| 6,479,691 B1 | * | 11/2002 | Sasaki et al. | ............... 558/321 |
| 6,559,085 B1 | * | 5/2003 | Sasaki et al. | ................ 502/22 |
| 6,642,405 B1 | | 11/2003 | Mori et al. | |
| 6,653,496 B1 | | 11/2003 | Mori et al. | |
| 6,740,769 B1 | * | 5/2004 | Mizutani et al. | ............ 558/324 |

FOREIGN PATENT DOCUMENTS

| | | |
|---|---|---|
| JP | 38-17967 | 9/1963 |
| JP | 38-19111 | 9/1963 |
| JP | 51-40391 | 4/1976 |
| JP | 59-204163 | 11/1984 |
| JP | 03/021346 | 1/1991 |
| JP | 06-009530 | 1/1994 |
| JP | 07-047272 | 2/1995 |
| JP | 07-051570 | 2/1995 |
| JP | 2640356 | 5/1997 |
| JP | 10-043595 | 2/1998 |
| JP | 10-066874 | 3/1998 |
| JP | 10-195036 | 7/1998 |
| JP | 10-231125 | 9/1998 |
| JP | 11-169715 | 6/1999 |
| JP | 2001-114740 | 4/2001 |
| WO | 01/28984 | 4/2001 |
| WO | WO 01/28984 A1 | 4/2001 |

* cited by examiner

*Primary Examiner*—Cam N. Nguyen
(74) *Attorney, Agent, or Firm*—Oblon, Spivak, McClelland, Maier & Neustadt, P.C.

(57) ABSTRACT

An ammoxidation catalyst comprising a molybdenum (component (1)), bismuth (component (2)), at least one element selected from the group consisting of nickel, cobalt, zinc, magnesium, manganese and copper (component (3)) and at least one element selected from the group consisting of lanthanum, cerium, praseodymium and neodymium (component (4)), over which an organic compound is subject to ammoxidation which is a composite oxide fluid bed catalyst, is prepared by i) preparing a first solution that comprises at least a portion of component (1), at least a portion of component (2), and at least a portion of component (3) but none of component (4); ii) preparing a second solution by adding a solution of component (4) to the first solution; and iii) drying the second solution obtained and calcining the solid matter obtained from the drying step.

12 Claims, No Drawings

METHOD FOR PRODUCING AMMOXIDATION CATALYST

TECHNICAL FIELD

The present invention relates to a method for preparing complex oxide-based catalysts used for ammoxidation of organic compounds.

BACKGROUND ART

As catalysts used for ammoxidation of organic compounds, various catalysts have hitherto been disclosed.

As catalysts for synthesis of acrylonitrile by ammoxidation of propylene, for example, Japanese Patent Application, Second Publication No. Sho 38-17967, discloses an oxide catalyst containing molybdenum, bismuth, and iron, while Japanese Patent Application, Second Publication No. Sho 38-19111, discloses an oxide catalyst containing iron and antimony.

These catalysts have been continuously and intensively improved and various catalysts containing rare earth elements as an essential component have been proposed.

For example, Japanese Patent Application, First Publication No. Sho 51-40391, Japanese Patent Application, First Publication No. Sho 59-204163, Japanese Patent Application, First Publication No. Hei 7-47272, Japanese Patent Application, First Publication No. Hei 7-51570, Japanese Patent Application, First Publication No. Hei 11-169715, Japanese Patent Application, First Publication No. 2000-5603 and Japanese Patent Application, First Publication No. 2001-114740 disclose catalysts containing molybdenum, bismuth, iron, and rare earth elements such as lanthanum, cerium, praseodymium and neodymium.

The Methods for preparing these catalysts have been studied so as to further improve the yield of the objective product.

For example, Japanese Patent Application, First Publication No. Hei 6-9530, discloses a method of heating a slurry containing molybdenum, bismuth, nickel, and cobalt at 90° C. for 3 hours, Japanese Patent No. 2520282 discloses a method of adjusting the pH of a slurry containing catalyst components to 5 or less, and Japanese Patent No. 2640356 discloses a method of adjusting the pH of a slurry containing molybdenum and iron to 5 or less and heat-treating the slurry at a temperature within a range from 50 to 120° C.

According to these methods for preparing a catalyst, some effect is exerted in respect of an improvement in yield of the target product and maintenance of reaction results for a long time; however, the effect is not industrially satisfactory. Therefore, it has been strongly desired to develop a catalyst which achieves high yield of the target product and can maintain high yield for a long time.

The present invention has been made to solve the problems described above, and an object of the present invention is to provide a method for preparing a catalyst which is useful for synthesis of nitrites by ammoxidation of organic compounds, especially synthesis of acrylonitrile by ammoxidation of propylene.

DISCLOSURE OF THE INVENTION

The present inventors have intensively researched to solve the problems described above and have found that, when respective feedstocks are mixed in a specific order in the preparation of a complex oxide-based catalyst used for ammoxidation of organic compounds, the yield of the objective product can be maintained at a high level for a long time. Thus, the present invention has been completed.

The method for preparing an ammoxidation catalyst of the present invention is directed to a method for preparing an ammoxidation catalyst comprising molybdenum (component (1)), bismuth (component (2)), at least one element selected from the group consisting of nickel, cobalt, zinc, magnesium, manganese and copper (component (3)), and at least one element selected from the group consisting of lanthanum, cerium, praseodymium and neodymium (component (4)), which is used for ammoxidation of an organic compound, said method comprising: a first solution preparing step of preparing a first solution which contains at least a portion of feedstocks of the component (1), at least a portion of feedstocks of the component (2) and at least a portion of feedstocks of the component (3), and does not contain feedstocks of the component (4), and a second solution preparing step of preparing a second solution by adding at least the feedstocks of the component (4) to the first solution.

Preferably, the method for preparing an ammoxidation catalyst of the present invention further comprises a heat treating step of heating the second solution to a temperature within a range from 50 to 120° C. for 10 minutes or more.

The pH of the second solution is preferably adjusted within a range from 1 to 6 before a heat treating step is conducted.

The ammoxidation catalyst preferably has a composition represented by the following empirical formula (I):

$$Mo_{10}Bi_aFe_bX_cCr_dE_eK_fG_gSb_hM_mZ_nO_x(S_iO_2)_y \quad (I)$$

wherein Mo, Bi, Fe, Cr, K, Sb and Si each represents molybdenum, bismuth, iron, chromium, potassium, antimony, and silicon, X represents at least one element selected from the group consisting of nickel, cobalt, zinc, magnesium, manganese and copper; E represents at least one element selected from the group consisting of lanthanum, cerium, praseodymium and neodymium; G represents at least one element selected from the group consisting of calcium, strontium, barium, cadmium, titanium, zirconium, vanadium, niobium, tantalum, tungsten, germanium, tin, yttrium, samarium, aluminum, gallium and lead; M represents at least one element selected from the group consisting of ruthenium, rhodium, palladium, rhenium, osmium, iridium, platinum, silver, boron, phosphorus and tellurium; Z represents at least one element selected from the group consisting of lithium, sodium, rubidium and cesium; O represents oxygen; subscripts a, b, c, d, e, f, g, h, m, n, x and y each represents an atomic ratio; when Mo=10, a=0.1 to 2.5, b=0.1 to 10, c=2 to 12, d=0.1 to 2.5, e=0.1 to 2.5, f=0.01 to 2, g=0 to 5, h=0 to 20, m=0 to 3, and n=0 to 1; x represents the number of oxygen atoms in a metal oxide produced by bonding the above respective components; and y=0 to 200.

Preferably, the ammoxidation catalyst is a catalyst for fluidized bed reaction and its composition is represented by the following formula (II):

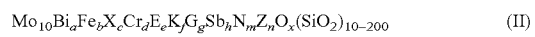

$$Mo_{10}Bi_aFe_bX_cCr_dE_eK_fG_gSb_hN_mZ_nO_x(SiO_2)_{10-200} \quad (II)$$

The organic compound is preferably propylene.

BEST MODE FOR CARRYING OUT THE INVENTION

The present invention will be described in more detail.

The ammoxidation catalyst prepared by the method of the present invention is a complex oxide-based catalyst which contains molybdenum (component (1)), bismuth (component (2)), at least one element selected from the group consisting of nickel, cobalt, zinc, magnesium, manganese and copper (component (3)), and at least one element selected from the group consisting of lanthanum, cerium, praseodymium and neodymium (component (4)), and is preferably used for ammoxidation of organic compounds such as olefin, alcohol, ether, aromatic compound and heterocyclic aromatic compound. The ammoxidation catalyst prepared by the method of the present invention may contain elements other than the components (1) to (4).

Specific examples of the organic compound include propylene, isobutene, methanol, ethanol, tertiary butanol, methyl tertiary butyl ether, toluene, xylene, picoline and chinaldine. The ammoxidation catalyst obtained by the method of the present invention is particularly suited for use in the case of synthesizing acrylonitrile by ammoxidation of propylene, and enables preparation of acrylonitrile at high yield and can maintain the high yield for a long time.

In the method for preparing ammoxidation catalyst of the present invention, first, a first solution preparing step of preparing a first solution, which contains at least a portion of feedstocks of molybdenum (component (1)), at least a portion of feedstocks of bismuth (component (2)) and at least a portion of feedstocks of at least one element selected from the group consisting of nickel, cobalt, zinc, magnesium, manganese, and copper (component (3)), and does not contain feedstocks of at least one element selected from the group consisting of lanthanum, cerium, praseodymium, and neodymium (component (4)), is conducted.

The feedstocks of the component (1) are not specifically limited and, for example, there can be used molybdenum oxides such as molybdenum trioxide; molybdic acids such as molybdic acid, ammonium paramolybdate and ammonium metamolybdate; ammonium salts of these molybdic acids; heteropoly acids containing molybdenum, such as phosphorus molybdic acid and silico molybdic acid; and salts of these heteropoly acids.

These feedstocks of the component (1) may be used in the form of a solid, or used after dissolving or dispersed in a solvent such as water.

The feedstocks of the component (2) are not specifically limited as far as they are metallic bismuth or compounds thereof and, for example, there can be used bismuth salts such as bismuth nitrate, bismuth carbonate, bismuth sulfate and bismuth acetate; and bismuth trioxide.

These feedstocks of the component (2) may be used in the form of a solid, or a solution in which the solid is previously dissolved in water or an aqueous nitric acid solution, or a slurry of a bismuth compound, which contains a solid deposited from the solution.

As the component (3), that is, feedstocks of at least one element selected from the group consisting of nickel, cobalt, zinc, magnesium, manganese and copper, for example, there can be used oxides thereof; nitrates, carbonates, organic acid salts and hydroxides which can be converted into oxides by calcination; and mixtures thereof.

In the first solution preparing step, at least a portion of feedstocks of the component (1) to (3) may be added without adding feedstocks of the component (4), and it is not necessarily to mix the total amount of the components (1) to (3). In that case, remaining feedstocks of the components (1) to (3) may be appropriately added at any stage which follows the first solution preparing step.

In the first solution preparing step, a first solution is prepared by using a solvent such as water. As the solvent, acid solutions such as aqueous nitric acid solution, and alkali solutions such as ammonia water may be optionally used, in addition to water. These solvents may be used after warming.

As long as a first solution, which does not contain feedstock of the component (4) and contains at least a portion of feedstocks of the components (1) to (3), is prepared, the method of mixing the components (1) to (3) and the order of mixing them are not specifically limited.

For example, a first solution may be prepared by dissolving or dispersing the respective feedstocks of the components (1), (2) and (3) in a solvent such as water and mixing the respective solutions or slurries, or a first solution may be prepared by adding a solvent to mixtures of the respective feedstocks of the components (1), (2), and (3) in the form of a solid.

When the ammoxidation catalyst prepared herein contains elements other than the components (1) to (4) (hereinafter referred to as a component (5)), all or a portion of the feedstocks may be mixed in the first solution preparing step.

As the feedstocks of the component (5), for example, there can be used oxides thereof; nitrates, carbonates, organic acid salts and hydroxides which can be converted into oxides by calcination; and mixtures thereof.

The first solution may be in the form of a solution in which the respective components are dissolved, or a slurry in which at least a portion of the respective components is not dissolved.

Then, a second solution preparing step of preparing a second solution by adding at least a component (4), that is, feedstock of one or more elements selected from the group consisting of lanthanum, cerium, praseodymium, and neodymium to the first solution obtained in the first solution preparing step.

In the second solution preparing step, as long as at least feedstock of the component (4) is added to the first solution, feedstocks of the component (5) may be optionally added, or the remainder of the feedstocks of the components (1) to (3) may be added. When the component (4) is added, solid feedstock thereof may be added to the first solution or may be added to the first solution after previously dissolving or dispersing in a solvent.

The form of the second solution varies depending on the composition of the objective ammoxidation catalyst and the kind of the compound used as feedstocks, and the second solution may be in the form of a solution in which the respective components are dissolved, or a slurry in which at least a portion of the respective components is not dissolved.

As described above, by conducting the second solution preparing step of adding at least feedstocks of the component (4) after the first solution preparing step, an ammoxidation catalyst capable of maintaining high yield of the objective product for a long time can be prepared.

The reason why such an effect is exerted is not yet clear, but is believed to be as follows. That is, formation of a catalyst structure or a catalyst precursor structure suited for ammoxidation is promoted by preparing a first solution which contains at least a portion of feedstocks of the component (1), at least a portion of feedstocks of the component (2) and at least a portion of feedstocks of the component (3) and does not contain feedstocks of the component (4) and adding at least feedstocks of the component (4).

Then, the pH of the second solution thus obtained is optionally adjusted within a range from 1 to 6.

Herein, the pH of the second solution may not be within a range from 1 to 6. However, when the pH is within a range from 1 to 6, the heat treating step described hereinafter can be effectively conducted and finally obtained ammoxidation catalyst enables preparation of the objective product at high yield. When the pH is less than 1 or more than 6, the yield of the target product sometimes decreases.

The lower limit of the pH of the second solution is preferably 1.5 and the upper limit is preferably 5.5. The pH can be increased by adding an aqueous alkali solution such as aqueous ammonia solution, and the pH can be decreased by adding an aqueous acidic solution such as an aqueous nitric acid solution.

As disclosed in Japanese Patent No. 2747920, chelating agents such as ethylenediaminetetraacetic acid, lactic acid, citric acid, tartaric acid and gluconic acid may be added to the first or second solution so as to suppress gelation of the second solution. The addition of these chelating agents is effective when gelation is likely to occur because of high pH. Even when the pH is adjusted to a comparatively low value ranging from 1 to 3, the addition of a small amount of the chelating agent sometimes exerts the effect of improving the yield and the activity of the objective product.

Then, a heat treating step of heating a second solution whose pH is optionally adjusted is preferably conducted. By conducting the heat treating step, the structure of the catalyst or the structure of the catalyst precursor becomes more stable, and thus a high-performance ammoxidation catalyst can be prepared with good reproducibility in a stable manner.

The heat treating step may be conducted under pressure or at atmospheric pressure. The treating temperature is not specifically limited and is preferably 50° C. or higher, and more preferably 80° C. or higher. When the treating temperature is lower than 50° C., the effect of the heat treating step is sometimes not exerted. The upper limit of the treating temperature is not specifically limited, and is usually 120° C. or lower when the heating treatment is conducted under atmospheric pressure. Since the treating time exerts insufficient effect when the treating time is too short, it is preferably 10 minutes or more, and more preferably 30 minutes or more. The upper limit of the treating time is not specifically limited and is usually less than 10 hours because the same effect is merely exerted even when the treatment is conducted for a long time more than is required.

After the heat treating step was conducted, feedstocks of the component (5) may be added, or the remainder of feedstocks of the components (1) to (3) which were not added in the previous stages may be added.

An ammoxidation catalyst can be obtained by drying and calcining the second solution.

The drying method is not specifically limited and a known method can be used. When the catalyst is used in the case of preparing acrylonitrile by ammoxidation of propylene, it is preferable to prepare generally spherical catalyst particles, which can be used in a fluidized bed, by drying the catalyst using a spray-drying method.

In the spray-drying method, common spray-drying apparatuses such as rotating disk type spray-drying apparatuses and nozzle type spray-drying apparatuses can be used. The spray-drying conditions are preferably set so that the resulting catalysts have a particle size within the range described hereinafter and can be used in a fluidized bed as long as the finally obtained ammoxidation catalyst can be used in a fluidized bed reactor.

Then, dried particles obtained by drying are calcined. The calcination method is preferably includes a low-temperature calcination process of calcining at a temperature within a range from 200 to 500° C. for 0.1 to 20 hours and the following high-temperature calcination process of calcining at a temperature within a range from 500 to 700° C. for 0.1 to 20 hours. When the calcination is conducted in two stages, that is, calcining at low temperature and calcining at high temperature, performances of the resulting ammoxidation catalyst are sometimes improved. As long as the calcination is conducted in two temperature ranges, that is, a low temperature range and a high temperature range, the calcination may be conducted multiple times at different temperatures within the respective temperature ranges.

Low-temperature calcination and high-temperature calcination are preferably conducted in an oxygen-containing gas atmosphere and can be conducted in an air and a mixed atmosphere of oxygen, nitrogen, carbon dioxide gas, and steam.

In the calcination, a box type calciner, a tunnel calciner, a rotary calciner and a fluidized bed calciner can be used. When the ammoxidation catalyst is used in a fluidized bed, a fluidized bed calciner is preferably used in final calcination.

The particle size of the catalyst thus prepared is preferably controlled within a range from 5 to 200 μm. The lower limit of the particle size is more preferably 10 μm, and the upper limit is more preferably 150 μm. The catalyst having a particle size within the above range is suited for use in a fluidized bed reactor because of its excellent fluidity.

The particle size is controlled by controlling the conditions of the drying described above. As used herein, the particle size does not refer to a mean particle size of the entire particles, but to a particle size of each particle.

The ammoxidation catalyst prepared by the method described above is not specifically limited as long as it is a complex oxide-based catalyst comprising molybdenum (component (1)), bismuth (component (2)), at least one element selected from the group consisting of nickel, cobalt, zinc, magnesium, manganese, and copper, (component (3)), and at least one element selected from the group consisting of lanthanum, cerium, praseodymium, and neodymium (component (4)), and is particularly preferably a catalyst with a composition represented by the following formula (I):

$$Mo_{10}Bi_aFe_bX_cCr_dE_eK_fG_gSb_hM_mZ_nO_x(SiO_2)_y \qquad (I)$$

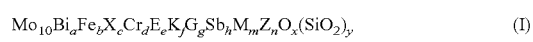

wherein Mo, Bi, Fe, Cr, K, Sb and Si each represents molybdenum, bismuth, iron, chromium, potassium, antimony, and silicon.

X represents at least one element selected from the group consisting of nickel, cobalt, zinc, magnesium, manganese, and copper, and nickel and/or cobalt are preferably contained as X.

E represents at least one element selected from the group consisting of lanthanum, cerium, praseodymium and neodymium, and lanthanum, and/or cerium are preferably contained as E.

G represents at least one element selected from the group consisting of calcium, strontium, barium, cadmium, titanium, zirconium, vanadium, niobium, tantalum, tungsten, germanium, tin, yttrium, samarium, aluminum, gallium, and lead.

M represents at least one element selected from the group consisting of ruthenium, rhodium, palladium, rhenium, osmium, iridium, platinum, silver, boron, phosphorus, and tellurium.

Z represents at least one element selected from the group consisting of lithium, sodium, rubidium, and cesium, and O represents oxygen.

Subscripts a, b, c, d, e, f, g, h, m, n, x and y each represents an atomic ratio. When Mo=10, the lower limit of a is preferably 0.1, more preferably 0.2, and the upper limit is preferably 2.5, more preferably 2.

The lower limit of b is preferably 0.1, more preferably 0.3, and the upper limit is preferably 10, more preferably 8.

The lower limit of c is preferably 2, more preferably 3, and the upper limit is preferably 12, more preferably 10.

The lower limit of d is preferably 0.1, more preferably 0.2, and the upper limit is preferably 2.5, more preferably 2.

The lower limit of e is preferably 0.1, more preferably 0.2, and the upper limit is preferably 2.5, more preferably 2.

The lower limit of f is preferably 0.01, more preferably 0.05, and the upper limit is preferably 2, more preferably 1.5.

x represents the number of oxygen atoms in a metal oxide produced by bonding the above respective components, and is a numerical value which is naturally decided.

The lower limit of g is 0 and the upper limit is preferably 5, the lower limit of h is 0 and the upper limit is preferably 20, the lower limit of m is 0 and the upper limit is preferably 3, and the lower limit of n is 0 and the upper limit is preferably 1. The lower limit of y is 0 and the upper limit is preferably 200. When the catalyst is used as a catalyst for fluidized bed reaction, y is preferably within a range from 10 to 200, and more preferably from 20 to 150 because it is possible to reconcile improvement of the strength of the catalyst and improvement in yield of the objective product.

When the catalyst is used as the catalyst for fluidized bed reaction, preferable composition of the catalyst component is represented by the following formula (II).

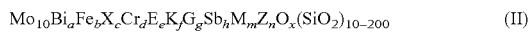

$$Mo_{10}Bi_aFe_bX_cCr_dE_eK_fG_gSb_hM_mZ_nO_x(SiO_2)_{10-200}$$ (II)

By preparing an ammoxidation catalyst having a composition represented by the formula (I) or (II) by the method described above, it is made possible to obtain a high-performance catalyst which achieves high yield of the objective product and can maintain high yield for a long time, and also is particularly suited for synthesis of acrylonitrile from propylene.

When the ammoxidation catalyst prepared herein contains iron and antimony, iron antimonate can also be used as feedstocks. When antimony and iron are contained in the catalyst in the form of iron antimonate, performance of the catalyst may be further improved.

Iron antimonate is a compound represented by the chemical formula $FeSbO_4$ described in Japanese Patent Application, First Publication No. Hei 4-118051 and Japanese Patent Application, First Publication No. Hei 10-231125, and can be identified by X-ray diffraction. Various methods for preparation of iron antimonate have been proposed. For example, the method may be appropriately selected from methods described in Japanese Patent Application, First Publication No. Hei 4-118051 and Japanese Patent Application, First Publication No. Hei 10-231125. Iron antimonate may contain a small amount of elements other than antimony and iron.

Iron antimonate is preferably added to the ammoxidation catalyst after preparing iron antimonate by the method disclose in the publications described above. Iron antimonate can be added in any stage of the process for preparation of the catalyst.

The resulting ammoxidation catalyst can be used as it is, or be used after supporting on a carrier.

When the ammoxidation catalyst is used for preparation of acrylonitrile due to ammoxidation of propylene, it is preferably used as a fluidized bed catalyst using silica as the carrier. When silica is used as the carrier, silica sol and fumed silica are used as feedstocks of silica. Among these carriers, silica sol is preferably used because of excellent handling properties.

Silica used as the carrier is preferably used within an element ratio of Si in the formulas (I) and (II), that is, 200 or less when Mo=10.

The ammoxidation catalyst prepared by the method of the present invention is used by filling in a fixed bed reactor or a fluidized bed reactor in the case of ammoxidation of various organic compounds.

In the case in which the reaction is conducted in a vapor phase, preferable reaction conditions are as follows: a feed gas has the composition of feedstock organic compound/ammonia/air=1/0.1 to 3/8 to 12 (molar ratio), the reaction temperature is within a range from 370 to 500° C., and the reaction pressure is within a range from atmospheric pressure to 500 kPa. The apparent contact time is within a range from 0.1 to 20 seconds. An air is used alone as an oxygen source and may be diluted with water vapor, nitrogen, carbon dioxide gas, saturated hydrocarbon or the like. Alternatively, the oxygen concentration may be increased by adding oxygen.

The method of preparing such an ammoxidation catalyst is a method for preparing an ammoxidation catalyst comprising molybdenum (component (1)), bismuth (component (2)), at least one element selected from the group consisting of nickel, cobalt, zinc, magnesium, manganese and copper (component (3)), and at least one element selected from the group consisting of lanthanum, cerium, praseodymium, and neodymium (component (4)), which is used for ammoxidation of an organic compound, said method comprising: a first solution preparing step of preparing a first solution which contains at least a portion of feedstocks of the component (1), at least a portion of feedstocks of the component (2) and at least a portion of feedstocks of the component (3), and does not contain feedstocks of the component (4), and a second solution preparing step of preparing a second solution by adding at least the feedstocks of the component (4) to the first solution. Therefore, it is made possible to prepare a high-performance catalyst which achieves high yield of the objective product and can maintain high yield for a long time.

By conducting the heat treating step of heating a second solution at a temperature within a range from 50 to 120° C. for 10 or more minutes, the structure of the catalyst or the structure of the catalyst precursor becomes more stable, and thus a high-performance ammoxidation catalyst can be prepared with good reproducibility in a stable manner.

Furthermore, by adjusting the pH of the second solution within a range from 1 to 6 before the heat treating step, the yield of the objective product is improved when using the finally obtained ammoxidation catalyst.

The ammoxidation catalyst prepared by such a method preferably has a composition represented by the above formula (I) or (II).

The ammoxidation catalyst obtained by such a method is suited for synthesis of acrylonitrile from propylene.

EXAMPLES

The present invention will be described in detail by way of examples and comparative examples. The present invention is not limited to the scope of examples.

[Test for Catalyst Activity]

Using ammoxidation catalysts prepared in the following examples and comparative examples, acrylonitrile was synthesized by ammoxidation of propylene. Then, activity of each catalyst was evaluated by determining yield of acrylonitrile. The yield of acrylonitrile was measured after 50 hours, 500 hours, and 1000 hours have passed since the beginning of the reaction.

The reaction conditions are as follows.

A catalyst was filled in a fluidized bed reactor having a catalyst fluidizing zone of an inner diameter of 25 mm and a height of 400 mm and a mixed gas having a composition of propylene/ammonia/air/water vapor=1/1.2/9.5/0.5 (molar ratio), as a reactant gas, was introduced therein at a linear velocity of the gaseous feedstock of 4.5 cm/sec. The reaction pressure was controlled to 200 kPa.

The contact time and yield of acrylonitrile shown in Table 1 are defined by the following equations.

Contact time(sec)=volume of catalyst in terms of apparent bulk density(ml)/feed gas flow rate(ml/sec)

The feed gas flow rate is a value calculated in terms of reaction conditions (temperature, pressure).

Yield of acrylonitrile(%)=(number of moles of produced acrylonitrile/number of moles of fed propylene)×100

Example 1

An ammoxidation catalyst with a composition represented by the following formula was prepared in the following manner.

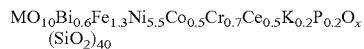
$Mo_{10}Bi_{0.6}Fe_{1.3}Ni_{5.5}Co_{0.5}Cr_{0.7}Ce_{0.5}K_{0.2}P_{0.2}O_x$ $(SiO_2)_{40}$ An atomic ratio x of oxygen is a value which is naturally decided by valences of the other elements. Hereinafter, its description is omitted.

300.7 g of ammonium paramolybdate was dissolved in 1000 g of pure water (solution A).

Separately, 49.6 g of bismuth nitrate, 272.4 g of nickel nitrate, 24.8 g of cobalt nitrate, 47.7 g of chromium nitrate and 3.4 g of potassium nitrate were dissolved in 270 g of 3.3% nitric acid (solution B).

The solution A was mixed in turn with 3.9 g of 85% phosphoric acid and the solution B to prepare a first solution. Subsequently, the first solution was mixed in turn with a solution prepared by dissolving 37.0 g of cerium nitrate in 100 g of pure water (solution C) and 2046.5 g of 20% silica sol and a solution prepared by dissolving 89.5 g of ferric nitrate and 20 g of citric acid in 270 g of pure water (solution D) to prepare a second solution.

To the resulting slurry-like second solution, 15% aqueous ammonia was added, thereby to adjust the pH to 2.0, followed by a heating treatment at 99° C. for 1.5 hours.

The resulting slurry was spray-dried using a rotary disk type spray drier under the conditions of an inlet temperature of 330° C. and an outlet temperature of 160° C. The resulting dried particles were heat-treated in an air atmosphere at 250° C. for 2 hours, then at 400° C. for 2 hours, and finally calcined in fluidized bed calciner at 650° C. for 3 hours.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 2

In the same manner as in Example 1, a catalyst with a composition represented by the formula: $Mo_{10}Bi_{1.0}Fe_{1.5}Ni_{4.0}Co_{1.0}Mg_{1.0}Cr_{0.4}Ce_{0.4}La_{0.3}K_{0.15}V_{0.05}(SiO_2)_{40}$ was prepared with the following exceptions.

85% phosphoric acid was not used, magnesium nitrate as feedstocks of magnesium was mixed with the solution B, lanthanum nitrate as feedstocks of lanthanum was mixed with the solution C, and ammonium metavanadate as feedstocks of vanadium was mixed with the solution A.

The pH was adjusted to 2.2 and the final calcination temperature was controlled to 640° C.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 3

In the same manner as in Example 1, a catalyst with a composition represented by the formula: $Mo_{10}Bi_{0.8}Fe_{0.9}Ni_{3.0}Mg_{2.0}Zn_{0.5}Cr_{0.8}Ce_{0.3}Pr_{0.1}K_{0.25}W_{0.1}(SiO_2)_{50}$ was prepared with the following exceptions.

Cobalt nitrate and 85% phosphoric acid were not used, magnesium nitrate as feedstocks of magnesium and zinc nitrate as feedstocks of zinc were mixed with the solution B, praseodymium nitrate as feedstocks of praseodymium was mixed with the solution C, and ammonium paratungstate as feedstocks of tungsten was mixed with the solution A.

The final calcination temperature was controlled to 640° C. The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 4

In the same manner as in Example 1, a catalyst with a composition represented by the formula: $Mo_{10}Bi_{0.5}Fe_{1.0}Ni_{2.0}Co_{4.0}Cr_{1.0}Ce_{0.4}La_{0.2}K_{0.1}Rb_{0.1}(SiO_2)_{40}$ was prepared with the following exceptions.

85% phosphoric acid was not used, lanthanum nitrate as feedstocks of lanthanum was mixed with the solution C, and rubidium nitrate as feedstocks of rubidium was mixed with the solution B.

The pH was adjusted to 1.8 and the final calcination temperature was controlled to 630° C.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 5

In the same manner as in Example 1, a catalyst with a composition represented by the formula: $Mo_{10}Bi_{0.3}Fe_{1.0}Ni_{3.0}Co_{3.0}Mg_{1.0}Cr_{0.5}Ce_{0.4}La_{0.4}K_{0.15}Sm_{0.1}Te_{0.2}Cs_{0.1}(SiO_2)_{40}$ was prepared with the following exceptions.

85% phosphoric acid was not used, magnesium nitrate as feedstocks of magnesium, samarium nitrate as feedstocks of samarium and cesium nitrate as feedstocks of cesium were mixed with the solution B, lanthanum nitrate as feedstocks of lanthanum was added to the solution C, and telluric acid as feedstocks of tellurium were mixed with the solution A.

The final calcination temperature was controlled to 640° C.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 6

In the same manner as in Example 1, a catalyst with a composition represented by the formula: $Mo_{10}Bi_{0.5}Fe_{1.1}Ni_{6.0}Cr_{0.6}Ce_{0.5}K_{0.2}P_{0.2}(SiO_2)_{60}$ was prepared with the following exception.

Cobalt nitrate was not used.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 7

In the same manner as in Example 1, a catalyst with a composition represented by the formula: $Mo_{10}Bi_{0.6}Fe_{1.1}Ni_{5.5}Co_{0.5}Mn_{0.2}Cr_{0.8}Ce_{0.4}K_{0.2}(SiO_2)_{40}$ was prepared with the following exceptions.

85% phosphoric acid was not used, and manganese nitrate as feedstocks of manganese was mixed with the solution B.

The pH was adjusted to 2.2 and the final calcination temperature was controlled to 640° C.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 8

A catalyst with a composition represented by the following formula: $Mo_{10}Bi_{0.4}Fe_{4.3}Ni_{5.5}Mn_{0.5}Cu_{0.2}Cr_{0.6}Ce_{0.4}Nd_{0.2}K_{0.1}Zr_{0.1}Sb_{3.5}P_{0.2}B_{0.2}Rb_{0.1}(SiO_2)_{40}$ was prepared in the following manner.

In 1000 g of pure water, 257.5 g of ammonium paramolybdate was dissolved (solution A).

Separately, 28.3 g of bismuth nitrate, 233.2 g of nickel nitrate, 20.9 g of manganese nitrate, 7.1 g of copper nitrate, 35.0 g of chromium nitrate, 1.5 g of potassium nitrate, 3.9 g of zirconium oxynitrate and 2.2 g of rubidium nitrate were dissolved in 270 g of 3.3% nitric acid (solution B).

The solution A was mixed in turn with 3.4 g of 85% phosphoric acid, 1.8 g of boric acid and solution B to prepare a first solution. Subsequently, the first solution was mixed in turn with a solution prepared by dissolving 25.3 g of cerium nitrate and 12.8 g of neodymium nitrate in 100 g of pure water (solution C) and 1752.2 g of 20% silica sol and a solution prepared by dissolving 64.8 g of ferric nitrate and 20 g of citric acid in 270 g of pure water (solution D) to prepare a second solution.

To the resulting slurry-like second solution, 15% aqueous ammonia was added, thereby to adjust the pH to 2.0, followed by a heating treatment at 99° C. for 1.5 hours.

To the slurry-like second solution after subjecting to the heating treatment, 290.5 g of a 40% iron antimonate slurry prepared separately by the method described hereinafter was added.

The resulting slurry was spray-dried using a rotary disk type spray drier apparatus under the conditions of an inlet temperature of 330° C. and an outlet temperature of 160° C. The resulting dried particles were heat-treated in an air atmosphere at 250° C. for 2 hours, then at 400° C. for 2 hours, and finally calcined in fluidized bed calciner at 650° C. for 3 hours.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

The iron antimonate slurry used herein was prepared in the following manner.

1815 g of nitric acid (65% by weight) was mixed with 1006 g of pure water, and 218.0 g of an electrolytic iron powder was added to the solution slowly. After iron powder was completely dissolved, the solution was mixed with 625.7 g of an antimony trioxide powder and 15% ammonia water was added dropwise while stirring, thereby to adjust the pH to 1.8. The resulting slurry was heated at 98° C. for 3 hours while stirring. The slurry was spray-dried using a spray drier under the conditions of an inlet temperature of 330° C. and an outlet temperature of 160° C., and calcined in an air atmosphere at 250° C. for 2 hours, then at 400° C. for 2 hours. Furthermore, the dried particles were calcined in a nitrogen gas flow at 850° C. for 3 hours. After calcination, the product was ground and then mixed with pure water to obtain a 40% iron antimonate slurry.

In the following examples, the iron antimonate slurry thus prepared was used.

Example 9

A catalyst with a composition represented by the following formula: $Mo_{10}Bi_{0.5}Fe_{1.3}Ni_{4.0}Co_{2.0}Cr_{0.8}Ce_{0.5}La_{0.1}K_{0.2}(SiO_2)_{40}$ was prepared in the following manner.

In 1000 g of pure water, 301.5 g of ammonium paramolybdate was dissolved (solution A).

Separately, 41.4 g of bismuth nitrate, 198.7 g of nickel nitrate, 99.4 g of cobalt nitrate, 54.7 g of chromium nitrate and 3.5 g of potassium nitrate were dissolved in 270 g of 3.3% nitric acid (solution B).

The solution A was mixed with the solution B to prepare a first solution. Subsequently, the first solution was mixed with a solution prepared by dissolving 37.1 g of cerium nitrate and 7.4 g of lanthanum nitrate in 100 g of pure water (solution C) and 2052.2 g of a 20% silica sol to prepare a second solution.

To the resulting slurry-like second solution, 15% aqueous ammonia was added, thereby to adjust the pH to 5.0, followed by a heating treatment at 99° C. for 1.5 hours. Separately, a solution was prepared by dissolving 89.7 g of ferric nitrate and 20 g of citric acid in 270 g of pure water (solution D) and then mixed with the slurry-like second solution after subjecting to the heating treatment.

The resulting slurry was spray-dried using a rotary disk type spray drier under the conditions of an inlet temperature of 330° C. and an outlet temperature of 160° C. The resulting dried particles were heat-treated in an air atmosphere at 250° C. for 2 hours, then at 400° C. for 2 hours, and finally calcined in fluidized bed calciner at 660° C. for 3 hours.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 10

In the same manner as in Example 9, a catalyst with a composition represented by the formula: $Mo_{10}Bi_{0.6}Fe_{1.3}Ni_{2.0}Co_{3.5}Cr_{0.7}Ce_{0.6}K_{0.25}P_{0.2}(SiO_2)_{40}$ was prepared with the following exception.

Lanthanum nitrate was not used, and 85% phosphoric acid as feedstocks of phosphorus was mixed with the solution A before mixing with the solution B. The pH was adjusted to 4.5 and the final calcination temperature was controlled to 630° C.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Example 11

A catalyst with a composition represented by the following formula: $Mo_{10}Bi_{0.5}Fe_{4.9}Ni_{3.0}Co_{2.0}Mg_{1.0}Cr_{0.6}Ce_{0.4}La_{0.1}K_{0.2}Sb_{4.2}P_{0.3}(SiO_2)_{40}$ was prepared in the following manner.

In 1000 g of pure water, 253.5 g of ammonium paramolybdate was dissolved (solution A).

Separately, 34.9 g of bismuth nitrate, 125.3 g of nickel nitrate, 83.6 g of cobalt nitrate, 36.8 g of magnesium nitrate, 34.5 g of chromium nitrate and 2.9 g of potassium nitrate were dissolved in 270 g of 3.3% nitric acid (solution B).

The solution A was mixed in turn with 5.0 g of 85% phosphoric acid and the solution B to prepare a first solution. Subsequently, the first solution was mixed in turn with a solution prepared by dissolving 24.9 g of cerium nitrate and 6.2 g of lanthanum nitrate in 100 g of pure water (solution C) and 1725.3 g of a 20% silica sol to prepare a second solution. To the slurry-like second solution, 15% aqueous ammonia was added, thereby to adjust the pH to 5.2, followed by a heating treatment at 99° C. for 1.5 hours. Separately, a solution was prepared by dissolving 63.8 g of ferric nitrate and 20 g of citric acid in 270 g of pure water (solution D) and then mixed with the slurry-like second solution after subjecting to the heating treatment.

Furthermore, the solution was mixed with 340.7 g of a 40% iron antimonate slurry prepared in the same manner as in Example 7.

The resulting slurry was spray-dried using a rotary disk type spray dryer under the conditions of an inlet temperature of 330° C. and an outlet temperature of 160° C. The resulting dried particles were heat-treated in an air atmosphere at 250° C. for 2 hours, then at 400° C. for 2 hours, and finally calcined in fluidized bed calciner at 650° C. for 3 hours.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Comparative Example 1

A catalyst with the same composition as in Example 1 was prepared in the same manner as in Example 1 with the following exception. Cerium nitrate was mixed with the solution B.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Comparative Example 2

A catalyst with the same composition as in Example 3 was prepared in the same manner as in Example 3 with the following exception. Cerium nitrate and praseodymium nitrate were mixed with the solution B.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Comparative Example 3

A catalyst with the same composition as in Example 4 was prepared in the same manner as in Example 4 with the following exception. Cerium nitrate and lanthanum nitrate were mixed with the solution B.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Comparative Example 4

A catalyst with the same composition as in Example 9 was prepared in the same manner as in Example 9 with the following exception. Cerium nitrate and lanthanum nitrate were mixed with the solution B.

The composition of the catalyst is shown in Table 1.

The solution containing feedstocks of the component (4) (element represented by E in the formulas (I) and (II)), pH of the second solution, conditions of the heat treating step, final calcination conditions, reaction conditions, and yield of acrylonitrile are shown in Table 2.

Using the ammoxidation catalysts obtained in the above examples and comparative examples, the ammoxidation reaction of propylene was conducted under the above reaction conditions and the catalysts were evaluated. The results are shown in Table 2.

| | Composition of catalyst (atomic ratio) | | | | | | | | | | | | | |
|---|---|---|---|---|---|---|---|---|---|---|---|---|---|---|
| | Mo | Bi | Fe | X | | | Cr | E | | K | G | Sb | M | Z | SiO$_2$ |
| Examples | | | | | | | | | | | | | | | |
| 1 | 10 | 0.6 | 1.3 | Ni 5.5 | Co 0.5 | | 0.7 | Ce 0.5 | | 0.2 | | | P 0.2 | | 40 |
| 2 | 10 | 1.0 | 1.5 | Ni 4.0 | Co 1.0 | Mg 1.0 | 0.4 | Ce 0.4 | La 0.3 | 0.15 | V 0.05 | | | | 40 |
| 3 | 10 | 0.8 | 0.9 | Ni 3.0 | Mg 2.0 | Zn 0.5 | 0.8 | Ce 0.3 | Pr 0.1 | 0.25 | W 0.1 | | | | 50 |
| 4 | 10 | 0.5 | 1.0 | Ni 2.0 | Co 4.0 | | 1.0 | Ce 0.4 | La 0.4 | 0.1 | | | | Rb 0.1 | 40 |
| 5 | 10 | 0.3 | 1.0 | Ni 3.0 | Co 3.0 | Mg 1.0 | 0.5 | Ce 0.4 | La 0.4 | 0.15 | | Sm 0.1 | Te 0.2 | Cs 0.1 | 40 |
| 6 | 10 | 0.5 | 1.1 | Ni 6.0 | | | 0.6 | Ce 0.5 | | 0.2 | | | P 0.2 | | 60 |
| 7 | 10 | 0.6 | 1.1 | Ni 5.5 | Co 0.5 | Mn 0.2 | 0.8 | Ce 0.4 | | 0.2 | | | | | 40 |
| 8 | 10 | 0.4 | 4.3 | Ni 5.5 | Mn 0.5 | Cu 0.2 | 0.6 | Ce 0.4 | Nd 0.2 | 0.1 | Zr 0.1 | 3.5 | P 0.2, B 0.2 | Rb 0.1 | 40 |
| 9 | 10 | 0.5 | 1.3 | Ni 4.0 | Co 2.0 | | 0.8 | Ce 0.5 | La 0.1 | 0.2 | | | | | 40 |
| 10 | 10 | 0.6 | 1.3 | Ni 2.0 | Co 3.5 | | 0.7 | Ce 0.6 | | 0.25 | | | P 0.2 | | 40 |
| 11 | 10 | 0.5 | 4.9 | Ni 3.0 | Co 2.0 | Mg 1.0 | 0.6 | Ce 0.4 | La 0.1 | 0.2 | | 4.2 | P 0.3 | | 40 |
| Comparative Examples | | | | | | | | | | | | | | | |
| 1 | 10 | 0.6 | 1.3 | Ni 5.5 | Co 0.5 | | 0.7 | Ce 0.5 | | 0.2 | | | P 0.2 | | 40 |
| 2 | 10 | 0.8 | 0.9 | Ni 3.0 | Mg 2.0 | Zn 0.5 | 0.8 | Ce 0.3 | Pr 0.1 | 0.25 | W 0.1 | | | | 50 |
| 3 | 10 | 0.5 | 1.0 | Ni 2.0 | Co 4.0 | | 1.0 | Ce 0.4 | La 0.2 | 0.1 | | | | Rb 0.1 | 40 |
| 4 | 10 | 0.5 | 1.3 | Ni 4.0 | Co 2.0 | | 0.8 | Ce 0.5 | La 0.1 | 0.2 | | | | | 40 |

TABLE 2

| | Method of mixing component E | pH | Heating treatment | | Calcination conditions | | Reaction conditions | | Yield of acrylonitrile [%] | | |
|---|---|---|---|---|---|---|---|---|---|---|---|
| | | | Temperature [°C.] | Time [hr] | Temperature [°C.] | Time [hr] | Temperature [°C.] | Contact time [sec] | After 50 h | After 500 h | After 1000 h |
| Examples | | | | | | | | | | | | |
| 1 | solution C | 2.0 | 99 | 1.5 | 650 | 3 | 440 | 3.0 | 82.9 | 82.5 | 81.7 |
| 2 | solution C | 2.2 | 99 | 1.5 | 640 | 3 | 440 | 2.7 | 82.3 | 82.0 | 81.2 |
| 3 | solution C | 2.0 | 99 | 1.5 | 640 | 3 | 440 | 3.2 | 83.1 | 82.4 | 81.2 |
| 4 | solution C | 1.8 | 99 | 1.5 | 630 | 3 | 440 | 3.0 | 82.5 | 81.9 | 81.2 |
| 5 | solution C | 2.0 | 99 | 1.5 | 640 | 3 | 440 | 3.0 | 82.6 | 81.8 | 81.1 |
| 6 | solution C | 2.0 | 99 | 1.5 | 650 | 3 | 440 | 2.8 | 83.0 | 82.4 | 81.6 |
| 7 | solution C | 2.2 | 99 | 1.5 | 640 | 3 | 440 | 2.6 | 82.7 | 82.1 | 81.0 |
| 8 | solution C | 2.0 | 99 | 1.5 | 650 | 3 | 440 | 3.2 | 82.1 | 81.5 | 80.9 |
| 9 | solution C | 5.0 | 99 | 1.5 | 660 | 3 | 440 | 3.0 | 82.8 | 82.3 | 81.6 |
| 10 | solution C | 4.5 | 99 | 1.5 | 630 | 3 | 440 | 2.7 | 82.4 | 81.7 | 80.9 |
| 11 | solution C | 5.2 | 99 | 1.5 | 650 | 3 | 440 | 3.2 | 82.5 | 81.9 | 81.1 |
| Comparative Examples | | | | | | | | | | | | |
| 1 | solution B | 2.0 | 99 | 1.5 | 650 | 3 | 440 | 3.0 | 83.0 | 81.9 | 80.8 |
| 2 | solution B | 2.0 | 99 | 1.5 | 640 | 3 | 440 | 3.2 | 82.9 | 81.5 | 80.3 |
| 3 | solution B | 2.0 | 99 | 1.5 | 630 | 3 | 440 | 3.0 | 82.3 | 80.8 | 79.7 |
| 4 | solution B | 5.0 | 99 | 1.5 | 660 | 3 | 440 | 3.0 | 82.6 | 81.3 | 80.1 |

As is apparent from Table 2, when using the ammoxidation catalysts obtained by the method of the examples, not only was acrylonitrile prepared at high yield after 50 hours had passed since the beginning of the reaction, but also the yield was maintained after 1000 hours had passed since the beginning of the reaction. The catalysts obtained in the comparative examples showed drastic reduction in yield of acrylonitrile over time.

INDUSTRIAL APPLICABILITY

As described above, according to the method for preparing an ammoxidation catalyst of the present invention, it is made possible to prepare a high-performance catalyst which achieves high yield of the objective product and can maintain high yield for a long time.

The ammoxidation catalyst obtained by the method of the present invention is particularly suited for synthesis of acrylonitrile from propylene.

The invention claimed is:

1. A method for preparing an ammoxidation catalyst comprising a molybdenum (component (1)), bismuth (component (2)), at least one element selected from the group consisting of nickel, cobalt, zinc, magnesium, manganese and copper (component (3)) and at least one element selected from the group consisting of lanthanum, cerium, praseodymium and neodymium (component (4)), whereby an organic compound can be subjected to ammoxidation over a composite oxide fluid bed catalyst comprising said catalyst, the method comprising:
   preparing a first solution which contains at least a portion of starting materials of component (1), at least a portion of starting materials of component (2), and at least a portion of starting materials of component (3), but no starting materials of component (4);
   preparing a second solution by adding at least starting materials of component (4) to the first solution; and
   adjusting the pH of the second solution to a value within a range of 1.5 to 5.5.

2. The method for preparing an ammoxidation catalyst according to claim 1, which further comprises a step of heating the second solution to a temperature ranging from 50 to 120° C.

3. The method for preparing an ammoxidation catalyst according to claim 2, wherein the heat treatment is conducted for at least 10 min.

4. The method for preparing an ammoxidation catalyst according to claim 1, further comprising drying the second solution by rotating disc spray-drying or by nozzle spray-drying to obtain dried particles.

5. The method for preparing an ammoxidation catalyst according to claim 4, wherein the dried particles obtained by spray-drying are calcined in a first low temperature calcination at 200 to 500° C. for 0.1 to 20 hours and followed by a high temperature calcination at 500 to 700° C. for 0.1 to 20 hours.

6. The method for preparing an ammoxidation catalyst according to claim 1, wherein the catalyst has a particle size ranging from 5 to 200 μm.

7. The method for preparing an ammoxidation catalyst according to claim 1, wherein the composite oxide ammoxidation catalyst has formula (I):

$$Mo_{10}Bi_aFe_bX_cCr_dE_eK_fG_gSb_hM_mZ_nO_x(S_iO_2)_y \quad (I)$$

wherein Mo, Bi, Fe, Cr, K, Sb and Si represent molybdenum, bismuth, iron, chromium, potassium, antimony and silicon; X represents at least one element selected from the group consisting of nickel, cobalt, zinc, magnesium, manganese and copper; E represents at least one element selected from the group consisting of lanthanum, cerium, praseodymium and neodymium; G represents at least one element selected from the group consisting of calcium, strontium, barium, cadmium, titanium, zirconium, vanadium, niobium, tantalum, tungsten, germanium, tin, yttrium, samarium, aluminum, gallium and lead; M represents at least one element selected from the group consisting of ruthenium, rhodium, palladium, rhenium, osmium, iridium, platinum, silver, boron, phosphorus and tellurium; Z represents at least one element selected from the group consisting of lithium, sodium, rubidium and cesium; O represents oxygen; and subscripts a, b, c, d, e, f, g, h, m, n, x and y each represents an atomic ratio such that when Mo=10, a=0.1 to 2.5, b=0.1 to 10, c=2 to 12, d=0.1 to 2.5, e=0.1 to 2.5, f=0.01 to 2, g=0 to 5, h=0 to 20, m=0 to 3 and n=0 to 1 and x is the number of oxygen atoms required to satisfy the total valences of the metal elements of the catalyst; and y=0 to 200.

8. The method for preparing an ammoxidation catalyst according to claim 7, wherein the composite oxide ammoxidation catalyst has formula (II):

$$Mo_{10}Bi_aFe_bX_cCr_dE_eK_fG_gSb_hN_mZ_nO_x(SiO_2)_{10-200} \quad (II)$$

wherein Mo, Bi, Fe, X, Cr, E, K, G, Sb, M, Z and O and $SiO_2$ are as defined above.

9. The method for preparing an ammoxidation catalyst according to claim 8, wherein the organic compound is propylene.

10. The method for preparing an ammoxidation catalyst according to claim 7, wherein the organic compound is propylene.

11. The method for preparing an ammoxidation catalyst according to claim 1, wherein the organic compound is propylene.

12. A method for preparing an ammoxidation catalyst comprising a molybdenum (component (1)), bismuth (component (2)), at least one element selected from the group consisting of nickel, cobalt, zinc, magnesium, manganese and copper (component (3)) and at least one element selected from the group consisting of lanthanum, cerium, praseodymium and neodymium (component (4)), whereby an organic compound can be subjected to ammoxidation over a composite oxide fluid bed catalyst comprising said catalyst, the method comprising:
   preparing a first solution which contains at least a portion of starting materials of component (1), at least a portion of starting materials of component (2), and at least a portion of starting materials of component (3), but no starting materials of component (4);
   preparing a second solution by adding at least the starting materials of component (4) to the first solution;
   adjusting the pH of the second solution to a value within a range of 1.5 to 5.5;
   drying the second solution to obtain dried particles; and
   calcining the dried particles obtained by spray-drying.

* * * * *